United States Patent [19]

Cannata et al.

[11] Patent Number: 4,661,628
[45] Date of Patent: Apr. 28, 1987

[54] PROCESS FOR THE OPTICAL RESOLUTION OF RACEMIC MIXTURES OF α-NAPHTHYL-PROPIONIC ACIDS

[75] Inventors: Vincenzo Cannata; Giancarlo Tamerlani, both of Pontecchio Marconi, Italy

[73] Assignee: Alfa Chemicals Italiana S.p.A., Milan, Italy

[21] Appl. No.: 668,301

[22] Filed: Nov. 5, 1984

[30] Foreign Application Priority Data

Nov. 23, 1983 [IT] Italy ............................... 3632 A/83

[51] Int. Cl.$^4$ .................. C07B 57/00; C07C 103/26; C07C 149/41; C07D 209/18; C07D 233/64
[52] U.S. Cl. .................................. 562/401; 548/342; 548/495; 560/56; 562/427; 562/469; 564/162; 564/172; 558/52
[58] Field of Search ............... 562/401; 564/172, 162; 260/456 P; 548/342, 495

[56] References Cited

U.S. PATENT DOCUMENTS

| | | |
|---|---|---|
| 3,651,106 | 3/1972 | Harrison ............... 562/401 |
| 3,683,015 | 8/1972 | Dyson ................. 562/401 |
| 3,686,183 | 8/1972 | Dyson ................. 562/401 |
| 3,904,682 | 10/1975 | Fried et al. ........... 562/401 |
| 3,904,683 | 9/1975 | Day et al. ............. 562/401 |
| 4,246,164 | 1/1981 | Felder et al. ......... 562/401 |
| 4,246,193 | 1/1981 | Holton ................ 562/401 |
| 4,399,284 | 8/1983 | Cannata et al. ....... 562/401 |

FOREIGN PATENT DOCUMENTS 0081993 6/1983 European Pat. Off.
2035846 12/1970 France.

OTHER PUBLICATIONS

Abstract of Japanese No. 56095-149, 12-28-1979.
Behrens et al, *Journal of Biological Chemistry*, vol. 175, pp. 771-792, (1948).

*Primary Examiner*—Natalie Trousof
*Assistant Examiner*—Vera C. Clarke
*Attorney, Agent, or Firm*—Bucknam and Archer

[57] ABSTRACT

A new process for the optical resolution of racemic mixtures of α-naphthyl-propionic acids of formula

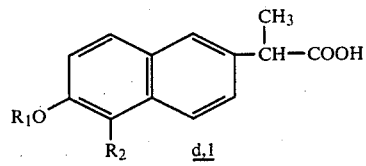

This process comprises reacting a racemic mixture of a compound of formula

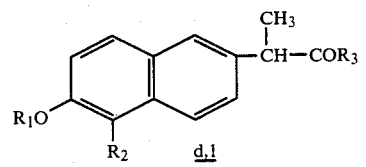

with an optically active substance of formula $R_4$—$NH_2$ (III), said substance being a β-aminoalcohol, thus forming a pair of diastereoisomeric amides which are resolved into the single diastereoisomers by fractional crystallization. The obtained single diastereoisomeric amide is then hydrolyzed to give the desired optically active α-naphthyl-propionic acid of formula

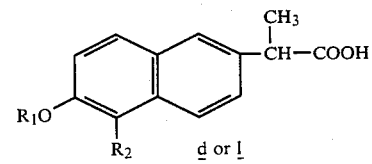

In the above compound I→III and VI, $R_1$ is $(C_{1-6})$alkyl, $R_2$ stands for hydrogen, halogen, mercapto, $(C_{1-6})$alkylthio, phenylthio, benzylthio, $(C_{1-6})$alkylsulfonyl, benzenesulfonyl, benzenesulfonyl substituted by halogen or $(C_{1-4})$alkyl, $R_3$ is a reactive group and $R_4$ is the residue of a primary or secondary alcohol.

27 Claims, No Drawings

PROCESS FOR THE OPTICAL RESOLUTION OF RACEMIC MIXTURES OF α-NAPHTHYL-PROPIONIC ACIDS

BACKGROUND OF THE INVENTION

The α-naphthyl-propionic acids are known from the literature for their biological properties. Owing to the presence of the asymmetric carbon atom bearing the naphthyl moiety, they can exist both as racemic mixtures and in the form of the corresponding d or l optically active isomers.

Of particular interest for its excellent antiphlogistic activity is the d isomer of the compounds of formula I, in which $R_1$ represents methyl and $R_2$ stands for hydrogen, namely the d-2-(6-methoxy-2-naphthyl)-propionic acid.

It was first described in U.S. Pat. No. 3,904,682 and is internationally known as naproxen.

Several methods for its preparation are reported in the art literature, including the patent literature. Typically, these methods contemplate the synthesis of d,l-2-(6-methoxy-2-naphthyl)-propionic acid, or a precursor thereof, and the subsequent resolution into the optical antipodes via formation of salts with optically active organic bases like cinchonidine, dehydroabietylamine, N-methyl-D-glucamine or, in general, N-alkyl-D-glucamins (see, for instance, French Publication No. 2,035,846 and U.S. Pat. Nos. 3,683,015; 4,246,164; 4,246,193 and 4,423,244). All of these resolution methods possess more or less severe drawbacks. As an example, it is often necessary to carry out several recrystallizations for obtaining the salt of the desired isomer in a pure form. In addition, their workability is considerably influenced by the purity degree of the material to be resolved.

Attempts for avoiding these drawbacks have led to stereospecific synthesis of naproxen and, in general, optically active α-naphthyl-propionic acids (see European laid open applications Nos. 81993 and 110671). To our experience, however, these procedures appear to involve a lot of problems, like the use of Grignard's reagents and the possibility of inversion of configuration.

Therefore, in the preparation of optically active α-naphthyl-propionic acids, there is still the need of valuable and economical resolution methods.

SUMMARY OF THE INVENTION

The present invention refers to a new process for the optical resolution of substantially racemic mixtures of α-naphthyl-propionic acids of formula

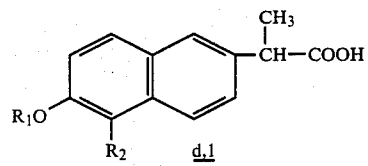

Briefly, the process comprises reacting a substantially racemic mixture of an α-naphthyl-propionic substrate of formula

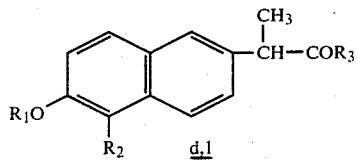

with a substance of formula $R_4$—$NH_2$, said substance being an optically active d- or l-β-aminoalcohol, whereby a pair of diastereoisomeric amides of formula

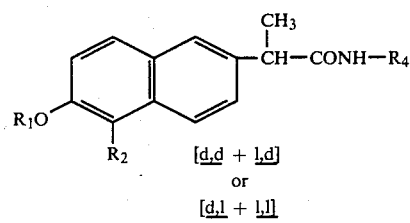

is formed. The pair of diastereoisomeric amides is then resolved into the corresponding single diastereoisomeric amides by fractional crystallization from a suitable solvent, optionally in the presence of a basic catalyst, and the recovered diastereoisomeric amide of the desired optically active α-naphthyl-propionic acid is finally subjected to acid hydrolysis.

The process which is the object of the present invention can be illustrated by the following scheme

SCHEME 1

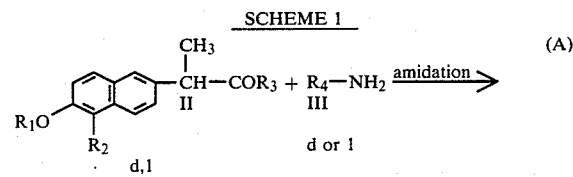

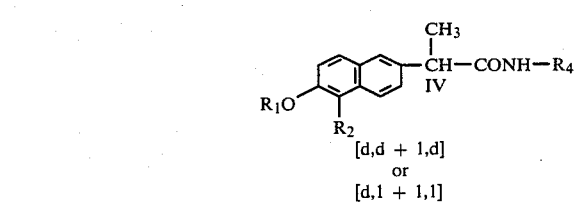

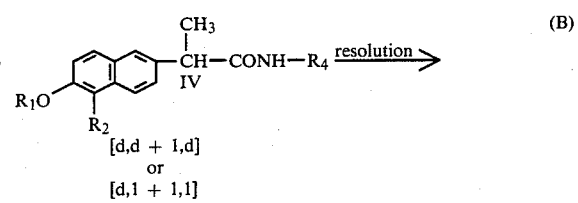

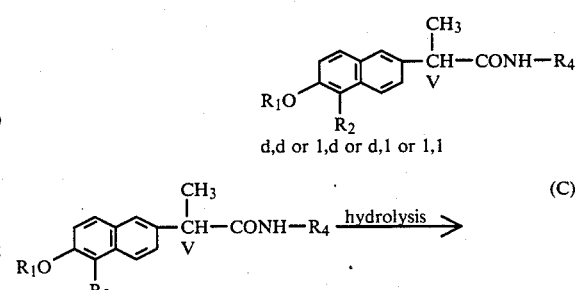

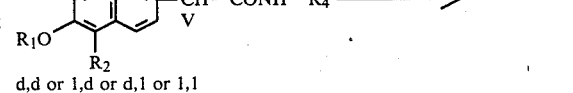

-continued
SCHEME 1

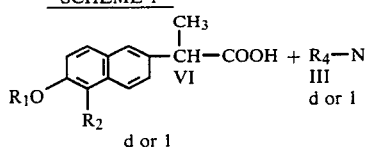

In the above formulas I to VI:

$R_1$ represents a $(C_{1-6})$alkyl radical;

$R_2$ stands for hydrogen, halogen, mercapto, $(C_{1-6})$alkylthio, phenylthio, benzylthio, $(C_{1-6})$alkylsulfonyl, benzenesulfonyl, benzenesulfonyl substituted by halogen or $(C_{1-4})$alkyl;

$R_3$ is a group selected from hydroxy; $(C_{1-8})$alkoxy; $(C_{1-8})$alkoxy substituted by halogen or phenyl or both; $(C_{2-6})$aliphatic acyloxy; benzoyloxy; substituted benzoyloxy; sulfonyloxy; $(C_{1-6})$alkylsulfonyloxy; benzenesulfonyloxy; 4-methyl-benzenesulfonyloxy; halogen; 2-imidazolyl-carbonyloxy;

$R_4$ is the residue of a primary or secondary alcohol which, taken together with the —$NH_2$ radical, forms an optically active d- or l-$\beta$-aminoalcohol, and is selected from the group

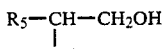

and the group

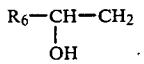

wherein $R_5$ stands for $(C_{1-6})$alkyl, primary hydroxy-$(C_{1-4})$alkyl, mercaptomethyl, methythioethyl, phenyl, hydroxyphenyl, phenylmethyl, hydroxyphenylmethyl, naphthyl, indolyl and imidazolyl, and $R_6$ stands for $(C_{1-6})$alkyl, phenyl, hydroxyphenyl, di-hydroxyphenyl and (4-hydroxy-3-methyoxy)-phenyl.

It will be also apparent for any person skilled in the art that, with reference to the diastereoisomeric amides of formula IV and V, the first letter of each of the pair of symbols d,d, l,d, d,l or l,l refers to the α-naphthyl-propionic acid portion, the second letter to the aminoalcoholic residue.

As used herein, the terms $(C_{1-4})$alkyl and $(C_{1-6})$alkyl designate linear or branched alkyl moieties from 1 to 4 and 1 to 6 carbon atoms respectively such as, for instance, methyl, ethyl, propyl, isopropyl, n-butyl, isobutyl, tert.-butyl, sec.-butyl, n-pentyl and n-hexyl as well as all the positional isomers thereof.

The terms $(C_{1-8})$alkoxy indicates linear or branched alkoxy groups like methoxy, ethoxy, propoxy, isopropoxy, n-butoxy, isobutoxy or tert.-butoxy, n-pentyloxy, neopentyloxy, or isopentyloxy, n-hexyloxy, 4-methylhexyloxy or 2-ethyl-butyloxy, 2-methyl-2-isopropyl-propoxy and 2-methyl-2butyl-propoxy. A $(C_{2-6})$aliphatic acyloxy group essentially designates acetoxy, propionyloxy, butyryloxy, isobutyryloxy, n-pentanoyloxy, pivaloyloxy and n-hexanoyloxy. The term halogen refers to fluorine, chlorine, bromine or iodine. A "substituted benzoyloxy" group is, for instance, 2-, 3-, or 4-chlorobenzoyloxy, 2-, 3- or 4-methylbenzoyloxy, 2-, 3- or 4-methoxybenzoyloxy or 3,4,5-trimethoxybenzoyloxy.

A preferred starting substrate of formula II is that wherein $R_1$ is $(C_{1-6})$alkyl, $R_2$ is hydrogen or halogen and $R_3$ is selected from hydroxy, $(C_{1-8})$alkoxy, $(C_{1-8})$alkoxy substituted by halogen or phenyl, or both, $(C_{2-6})$aliphatic acyloxy, benzoyloxy and halogen.

A most preferred starting substrate of formula II is that wherein $R_1$ is $(C_{1-6})$alkyl, $R_2$ is hydrogen or halogen and $R_3$ is selected from $(C_{1-8})$alkoxy, $(C_{1-8})$alkoxy substituted by halogen or phenyl, or both, and halogen.

According to the above Scheme 1, the first step of the resolution method of the invention is the formation of a pair of diastereoisomeric amides, by reaction of substantially racemic mixture of an α-naphthyl-propionic substrate of formula

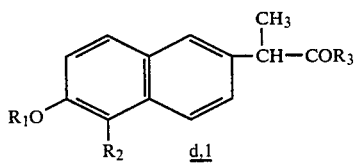

wherein $R_1$, $R_2$ and $R_3$ are as above defined, with a substance of formula $R_4$—$NH_2$, said substance being an optically active d- or l-$\beta$-aminoalcohol, in which $R_4$ is as above defined. Several optically active $\beta$-aminoalcohols proved to be useful for the invention purposes and, accordingly, the new resolution process herein described will not be limited by the choice of the substance $R_4$—$NH_2$. Preferred optically active $\beta$-aminoalcohols which give particularly satisfactory results are those in which $R_4$ represents the moiety

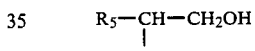

or the moiety

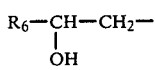

and $R_5$ and $R_6$ are a $(C_{1-6})$alkyl radical as above defined, e.g. d- and 1-2-amino-1-propanol ($R_5$=methyl), d- and 1-2-amino-1-butanol ($R_5$=ethyl), d- and 1-2-amino-3-methyl-1-butanol ($R_5$=isopropyl), d and 1-2-amino-4-methyl-1-pentanol ($R_5$=isobutyl), d- and 1-2-amino-1-pentanol ($R_5$=propyl), d- and 1-2-amino-1-hexanol ($R_5$=n-butyl), d- and 1-2-amino-1-heptanol ($R_5$=n-pentyl), d- and 1-2-amino-1-octanol ($R_5$=n-hexyl), d- and 1-2-amino-3,3-dimethyl-1-butanol ($R_5$=tert.-butyl), d- and 1-1-amino-2-propanol ($R_6$=methyl), d- and 1-1-amino-2-butanol ($R_6$=ethyl), d- and 1-1-amino-3-methyl-2-butanol ($R_6$=isopropyl), d- and 1-1-amino-3,3-dimethyl-2-butanol ($R_6$=tert.-butyl), d- and 1-1-amino-2-pentanol ($R_6$=propyl), d- and 1-1-amino-4-methyl-2-pentanol ($R_6$=isobutyl), d- and 1-1-amino-2-hexanol ($R_6$=n-butyl), d- and 1-1-amino-2-heptanol ($R_6$=n-pentyl) and d- and 1-1-amino-2-octanol ($R_6$=n-hexyl).

Other preferred optically active $\beta$-aminoalcohols of formula $R_4$—$NH_2$ are those in which $R_4$ represents the moiety

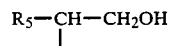

and the moiety

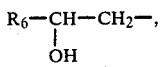

wherein R₅ and R₆ stand for phenyl or hydroxyphenyl, namely d- and l-2-amino-2-phenyl-ethanol (R₅=phenyl), d- and l-2-amino-2-(4-hydroxyphenyl)-ethanol (R₅=4-hydroxyphenyl), d and l-2-amino-1-phenylethanol (R₆=4-hydroxyphenyl), d- and l-2-amino-5-(3-hydroxyphenyl)-ethanol (R₆=3-hydroxyphenyl).

Other optically active β-aminoalcohols which are particularly useful for the invention purposes are d- and l-2-amino-3-phenyl-1-propanol-, d- and l-2-amino-3-(4-hydroxyphenyl)-1-propanol, d- and l-2-amino-3-mercapto-1-propanol, d- and l-2-amino-4-methylthio-1-butanol, d- and l-2-amino-2-(1-naphthyl)-ethanol, d- and l-2-amino-3-(3-indolyl)-1-propanol, d- and l-2-amino-3-4(5)-imidazolyl)-1-propanol, d- and l-2-amino-1-(3,4-dihydroxyphenyl)-ethanol and d- and l-2-amino-1-(4-hydroxy-3-methoxy)-ethanol.

Though not herein expressly mentioned, other optically active β-aminoalcohols corresponding to the general formula R₄—NH₂, in which R₄ is defined as above, are intended to fall within the purposes of the present invention.

In the actual practice, a molar proportion of a substantially racemic mixture of a compound of formula II above is reacted with from about 1 to about 10 molar proportions of an optically active d- or l-β-aminoalcohol of formula III, optionally in the presence of an organic solvent, at a temperature comprised between about room temperature and the boiling temperature of the reaction mixture.

Suitable reaction solvents are represented by (C₆₋₉) linear or cyclic hydrocarbons, aromatic hydrocarbons like benzene, toluene, the xylenes, nitrobenzene and analogs, halogenated (C₁₋₄) hydrocarbons, e.g. methylchloride, methylenechloride, chloroform, carbon tetrachloride, bromoform, methylene bromide, 1,1,2,2-tetrachloroethane and analogs, tetrahydrofuran, di-hydropyran, tetrahydropyran, ethylene or propylene glycol and the corresponding mono- or di-(C₁₋₂)alkyl ethers, lower aliphatic ketones like acetone, methylethylketone, methylisobutylketone and analogs, ethylacetate, butylacetate and analogs, or mixtures thereof.

Preferred solvent are the halogenated (C₁₋₄) hydrocarbons and the aromatic hydrocarbons.

The temperature at which the amidation reaction as per step (A) of the above Scheme is carried out is not critical. As stated above, it may vary within about the room temperature and the boiling temperature of the reaction mixture. It was observed that, when an α-naphthyl-propionic acid halide is used as the starting substrate, the amidation reaction runs satisfactorily at about room temperature, whereas more drastic temperature conditions are required when, in the starting compound of formula II, R₃ represents a (C₁₋₈)alkoxy radical, optionally substituted by halogen or phenyl or both. These drastic conditions, however, can be avoided if the reaction is carried out in the presence of strong basic agents such as, for instance, ammonium hydroxide, an alkali metal or alkaline earth metal hydride or amide, or an alkali metal (C₁₋₄)alkoxide. The basic agent can be added in amounts varying within very wide limits. Preferably, it is added in an amount comprised between about 3 and about 15 molar percent, calculated over the starting substrate of formula II. In this case, the amidation reaction can advantageously take place at a temperature comprised between about room temperature and about 50° C.

If an α-naphthyl-propionic acid halide of formula II (R₃=halogen) is selected as the starting substrate, the presence of an organic base may be necessary in order to neutralize the acid which forms during the reaction. The organic base may be the preselected optically active d- or l-β-aminoalcohol itself or a tertiary organic base like the tri-(C₁₋₄)alkylamines, pyridine, the pycolines and the like.

The yields of this step are pratically quantitative in any case never lower than 90%. A pair of diastereoisometric amides of formula

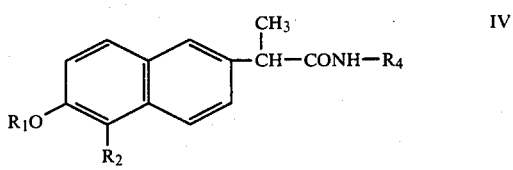

wherein R₁, R₂ and R₄ are as above defined, is formed, which depending on whether the selected optically active β-aminoalcohol is the d or l-isomer, can be the pair [d,d+l,d] or the pair [d,l+l,l]. The so obtained pair of diastereoisomeric amides can be isolated and characterized, if desired, or directly subjected to the resolution into the single diastereoisomeric amides according to step (B) of the above reaction Scheme.

This step is performed by dissolving or suspending the selected pair of diastereoisomeric amides of formula IV in a solvent or solvent system, heating these mixtures to a predetermined temperature, and gradually cooling the obtained solution, thus causing the less soluble of the two diastereoisomeric amides to precipitate from the reaction medium. Several solvents or solvent systems can advantageously be employed in this resolution step such as, for instance, the same media used in the above illustrate amidation procedure. Other solvents or solvent systems which have given absolutely satisfactory results are the polar solvents like the lower aliphatic ketones and the N,N-di-(lower alkyl)-amides of lower aliphatic acids, e.g. acetone, methylethylketone methylisopropylketone, diethylketone, methylisobutylketone, dimethylformamide, diethylformamide, dimethylacetamide and analogs, alone or in admixture with water in various volumetric ratios. The choice of the solvent or solvent system is not critical, though it may depend on the nature of the substrate of formula III to be resolved. In general, the solvent, or the solvent system is selected so as to provide the maximum difference in solubility between the single diastereoisomeric amides.

To illustrate, the resolution step can be performed by suspending at room temperature the selected pair of diastereoisomeric amides of formula IV, in a solvent or solvent system, which is advantageously selected from an aromatic hydrocarbon like benzene, toluene, the xylenes or nitrobenzene, a lower aliphatic ketone or an N,N-di-(lower alkyl)-amide of a lower aliphatic acid, alone or in admixture with water, or from ethylene or propylene glycol and the corresponding mono- or di-(C₁₋₂)alkylethers. The reaction mixture is then heated until the solid is almost completely dissolved and the resulting mixture is gradually cooled. In order to favor the fractional crystallization of the desired single diastereoisomeric amide the reaction mixture can be seeded, at a predetermined temperature, with a small amount of crystals of the desired diastereoisomeric amide. The temperature at which the seeding occurs may be dependent on the nature of the solvent or solvent system; as an example, when an aromatic hydrocarbon, like toluene, is the employed solvent, seeding may take place at about 85°–80° C., whereas, when the solvent system is a lower aliphatic ketone, like acetone or an N,N-di-(lower alkyl)-amide of a lower aliphatic acid such as, for instance, dimethylformamide, in admixture with water, seeding may occur at about 35°–30° C. In general, seeding occurs as soon as the desired precipitate begins to form.

The reaction mixture can advantageously be kept at the seeding temperature for a period of time varying from about 1 to about 3 hours, then it is gradually cooled until complete precipitation of the desired single diastereoisomeric amide. Depending on the nature of the employed solvent or solvent system, the final temperature is comprised between about 40° C. and about room temperature or less. In general, the resolution is performed in a period of time varying from about 3 to about 6 hours.

The diastereoisomeric amide which precipitates is in a pratically pure crystalline form. With reference to the above reaction scheme, it can be one of the following four amides, namely d,d; l,d; d,l or l,l, wherein the first letter of each pair pertains to the α-naphthyl-propionic acid portion, the second letter to the aminoalcoholic residue. The yields of desired diastereoisomeric amide are absolutely satisfactory: they are generally higher than 40%, if calculated over the pair of diastereoisomeric amides, or higher than 80%, if calculated over the single diastereoisomeric amide present in the pair.

A preferred mode of performing the resolution step (B) comprises first dissolving or suspending the selected pair of diastereoisomeric amides of formula IV [d,d+l,d] or [d,l+l,l] in a suitable solvent or solvent system such as, for instance, an aromatic hydrocarbon as defined above, a halogenated ($C_{1-4}$) hydrocarbon, ($C_{1-6}$) lower alkanols, tetrahydrofuran, dihydropyran, tetrahydropyran and analogs, or mixtures thereof. The so obtained solution or suspension is then heated, preferably to the boiling temperature of the employed medium, whereby, in case of a suspension, the solid dissolves almost completely.

The resulting mixture is gradually cooled to a predetermined temperature interval, a catalytic amount of a strong alkali agent is added and the mixture is kept within said temperature interval for a period of time varying from about 6 to about 30 hours. This temperature interval is not critical and essentially depends on the employed solvent or solvent system. As an illustrative, though not limitative example, when the solvent is an aromatic hydrocarbon like toluene, the addition of the alkaline agent occurs in the temperature interval comprised between about 75° and about 50° C. Suitable strong basic agents are selected from ammonium hydroxide, alkali lower alkoxides such as, for instance, sodium methoxide, sodium ethoxide, potassium methoxide, sodium isopropoxide, potassium tert.-butoxide and the like, alkali or earth-alkali hydrides, e.g. sodium or potassium hydride or magnesium or calcium hydride, alkali or earth-alkali amides like sodium amide, potassium amide, calcium amide and analogs. The amount of basic catalyst to be added may vary within very wide ranges. Preferred amounts are comprised between about 3 and about 10 molar percent calculated over the pair of diastereoisomeric amides of formula IV to be resolved. They are preferably added under an inert gas atmosphere, e.g. under nitrogen atmosphere.

As stated above, after the addition of the catalyst, the reaction mixture is kept within the predetermined temperature interval for a period of time varying from about 6 to about 30 hours, whereby most of the desired single diastereoisomeric amide crystallizes out from the medium.

A further gradual cooling completes the crystallization of the desired end product, which is recovered by filtration. The final temperature is advantageously selected from about 45° C. to about room temperature or less.

It has also been found that, in order to favor the fractional precipitation of the desired single diastereoisomeric amide, the reaction solution can be seeded with a small amount of crystals of the same amide. For the purposes of the present invention, seeding can take place before or after the addition of the basic catalyst.

The single diastereoisomeric amides d,d or l,d or d,l or l,l obtained through the above illustrated resolution method may undergo, if necessary, a purification in order to make them free from any impurity. This purification can be achieved by recrystallization from suitable solvents, e.g. those employed in the resolution procedure, to which a small amount of a weak acidic agent such as, for instance, acetic acid, may be added. If desired, said purification can be performed before bringing the reaction mixture to the above final temperature. To this purpose, after addition of the weak acidic agent, the reaction mixture is heated until complete dissolution is observed. Then, upon cooling to the suitable final temperature, the desired single diastereoisomeric amide crystallizes out in a practically pure form.

The yields of single diastereoisomeric amide achieved by this procedure are exceptionally high. In fact, they are never lower than 70%, but calculated over the starting pair of diastereoisomeric amides, not over the single diastereoisomeric amide contained in the pair. In other words, one molar amount of a pair of diastereoisomeric amides [d,d+l,d] or [d,l+l,l] is resolved so as to provide not the maximum expected amount of the single diastereoisomer, namely 0.5 moles, but at least 0.7 molar equivalents.

That amides of substantially racemic mixtures of α-naphthyl-propionic acids with optically active d- or l-β-aminoalcohols could be resolved by fractional crystallization is a totally new teaching. Certain amides of racemic α-naphthyl-propionic acids are described in Dutch laid open application No. 75 12107, where it is also stated that they can be resolved into the corresponding optical antipodes. Apart from the fact that no example is reported of amides with any aminoalcohol, the resolution could theoretically (as, again, no concrete example was reported) be achieved in a completely different manner i.e., by the enzymatic route or by formation of diatereoisomeric salts with optically active organic bases like cinchonidine and subsequent fractional crystallization of those salts.

In Japanese Publication pre-examination No. 56 095149, an attempt is described for resolving the d,l-2-(6-methoxy-2-naphthyl)-propionic acid into the corresponding optical antipodes, by subjecting to chromatographic separation a corresponding amide with an optically active β-aminoethanol derivative. Also this method, however, has little to do with the resolution process of the present invention and, to the art skilled technician, it appears rather speculative in view of the high costs, times and volumes involved in a chromatographic procedure carried out on industrial scale. As a matter of fact, no concrete examples on how the chromatographic resolution is performed are actually reported.

In addition to these considerations, it must also be pointed out that when the resolution process of the present invention is performed in the presence of a strong basis agent, it is possible to obtain the final precursors of the desired optically active α-naphthyl-propionic acids of formula

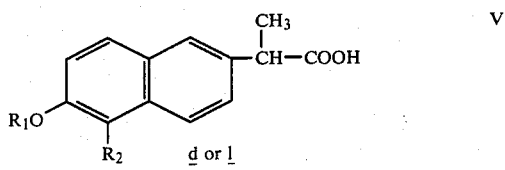

with yields which are absolutely higher than those obtained with the classical resolution methods known from the art literature. In fact, in none of these procedures, all based on the formation of pairs of diastereoisomeric salts with optically active organic bases, the desired single diastereoisomeric salt is obtained with a yield higher than 50%, when calculated over the pair of salts which must be resolved.

As stated above, step (B), namely the resolution, can advantageously be carried out without isolating the pair of diastereoisomeric amides of Formula IV prepared according to step (A). In this respect, the exceptionally good yields of the desired single diastereoisomeric amide are also achieved when the racemic substrate of formula III and the optically active d- or l-β-aminoalcohol are contacted in the presence of from about 3 to about 15 molar percent, of the above basic agents, calculated over the compound of formula III, and the amidation and resolution steps are performed as above described. In a representative, though not limitative example, in which in the substrate of formula II $R_3$ is $(C_{1-8})$alkoxy, $R_1$ is methyl and $R_2$ is hydrogen and the optically active d- or l-βaminoalcohol is the d-2-amino-1-butanol and the basic catalyst is an alkali alkoxide, the diastereoisomeric amide N-[d-2-(1-hydroxy)-butyl]-d-2-(6-methoxy-2-naphthyl)-propionamide was obtained with a yield higher than 80%, calculated over the starting racemic substrate.

Considering also that the yields of the subsequent hydrolytic step (C) are always higher than 90%, it is clear that the present invention provides a new and useful method for the preparation of optically active α-naphthyl-propionic acids.

The amides of formula IV, both as pair of diastereosiomeric compounds or in the form of the single diastereoisomers of formula V are new and, accordingly, they represent a further object of the invention.

To obtain the final compounds of formula VI the selected single diastereoisomeric amide of formula V obtained as under step B) is subjected to acidic hydrolysis, as an example, by means of concentrated or diluted mineral acids, and, if necessary, to a further purification procedure in order to obtain the desired end product with the maximum purity degree. Said purification, however, has absolutely no influence on the yields of this step.

When a compound of formula VI is obtained, in which $R_2$ is halogen, mercapto, $(C_{1-6})$alkylthio, phenylthio, benzylthio, $(C_{1-6})$alkylsulfonyl, benzenesulfonyl, benzenesulfonyl substituted by halogen or $(C_{1-4})$alkyl, it is possible to catalytically remove these groups so as to restore the hydrogen atom. For instance, this can be achieved by means of the hydrogenation procedure described in U.S. Pat No. 4,423,244. It has also been found that, when the removal of these groups is carried out on a pair of diastereoisomeric amides of formula IV, a concomitant fractional crystallization may occur, so that the end product may be one of the single diastereoisomeric amides present in the starting pair, in which $R_2$ is hydrogen. Other obvious methods for replacing the above said groups with a hydrogen atom will be apparent to the art skilled technician. Anyway, these groups can be removed at any step of the above illustrated reactions sequence without any prejudice for the reactions themselves and the entire results of the process.

The following examples are provided for with the purpose of better illustrating the invention. The determination of the optical rotatory power was carried out by means of a Perkin Elmer 241 apparatus. The starting substrates of formula II are prepared by literature methods. The optically active β-aminoalcohols of formula III are commercial products or are prepared by literature methods.

EXAMPLE 1

N-[d-2-(1-Hydroxy)-butyl]-d,l-2-(6-methoxy)-2-naphthyl)-propionamide[d,d+l,d]-203 Grams (0.815 mole) of d,l-2-(6-methoxy-2-naphthyl)-propionic acid chloride in 500 ml of methylene chloride were dripped into a solution of 164 ml (1.74 mole) of d-2-amino-1-butanol in 1000 ml of methylene chloride at room temperature. After 15 minutes, the reaction mixture was treated with 1000 ml of water and acidified to pH 2 by means of 6N aqueous hydrochloric acid. The organic layer was separated, washed with water until neutrality and subsequently dried over sodium sulfate. After evaporation of the solvent, an oily residue was obtained, which was taken up with 500 ml of tetrachloroethylene. Upon filtration 213.9 g (87%) of the title compound were obtained. $[\alpha]_D^{20} = -32.5°$ (C=1% in methanol). m.p. 105°–126.5° C.

EXAMPLE 2

N-[l-2-(1-Hydroxy)-butyl]-d,l-2-(6-methoxy-2-naphthyl)-propionamide[d,l−l,l]

A solution of 200 g (0,803 mole) of d,l-2-(6-methoxy-2-naphthyl)-propionic acid chloride in 500 ml of methylene chloride was dripped into a solution of 73.8 ml (0.78 mole) of l-2-amino-1-butanol and 108.7 ml (0.78 mole) of triethylamine in 500 ml of methylene chloride, at room temperature. After 30 minutes, the reaction mixture was treated with 1000 ml of water, whereby a solid began to form. This solid was dissolved by gentle heating, the solution was then cooled, the organic layer was separated, washed with water and dried over sodium sulfate. After evaporating the solvent, a residue was obtained, which was worked up as described in the foregoing Example. Yield: 205.4 g (85%) of the title compound. $[\alpha]_D^{20} = +31.2°$ (C=1% in methaol). m.p. 102°–125° C.

EXAMPLE 3

N-[l-2-(1-Hydroxy)-butyl]-d,l-2-(6-methoxy-2-naphthyl)-propionamide[d,l+l,l]

10 Grams (0.041 mole) of d,l-2-(6-methoxy-2-naphtyl)-propionic acid methyl ester were admixed with 20 ml (0.212 mole) of l-2-amino-1-butanol and the resulting mixture was heated for 8 hours at 130° C. under nitrogen atmosphere. After cooling to room temperature and adding 100 ml of water, the solution was brought to pH 2 by means of 6N aqueous hydrochloric acid. A solid was obtained, which was filtered, washed with water and recrystallized from tetrachloroethylene. Yield: 10.7 g (86.8%). $[\alpha]_D^{20} = +31.2$ (C=1% in methanol). m.p. 102°–125° C.

EXAMPLE 4

N-[d-2-(1-Hydroxy)-butyl]-d,l-2-(5-bromo-6-methoxy-2-naphthyl)-propionamide[d,d+l,d]

154.6 Grams (0.471 mole) of d,l-2-(5-bromo-6-methoxy-2-naphthyl)-propionic acid chloride were dissolved in 500 ml of methylene chloride and the obtained solution was slowly dripped into a solution of 47.2 ml (0.50 mole) of d-2-amino-1-butanol and 104 ml (0.74 mole) of triethylamine in 500 ml of methylene chloride, at room temperature. After 15 minutes the reaction mixture was treated with 1000 ml of water, then the pH was brought to 2 by means of 6N aqueous hydrochloric acid, whereby a solid was obtained which was washed with water, then with methylene chloride and finally dried. Yield: 163.6 g (91.3%) of title compound. $[\alpha]_D^{20} = -25.5°$ (C=1% in methanol). m.p. 143°–147° C.

EXAMPLE 5

N-[l-2-(1-Hydroxy)-butyl]-d,l-2-(5-bromo-6-methoxy-2-naphthyl)-propionamide[d,l+l,l]

48.2 Grams (0.105 mole) of d,l-2-(5-bromo-6-methoxy-2-naphthyl)-propionic acid 3-bromo-2,2-dimethyl-propyl ester were suspended in 75 ml (0.795 mole) of l-2-amino-1-butanol, and the reaction mixture was heated at 130° C. for 16 hours under nitrogen atmosphere. After cooling to room temperature, the mixture was treated with 200 ml of methylene chloride and 400 ml of water, then the pH was brought to 2 by means of 6N aqueous hydrochloric acid. A suspension was obtained, which was cooled to 10° C., the formed solid was filtered, washed first with water and then with methylene chloride and finally recrystallized from ethyl acetate. Yield: 34 g (85%) of title product. $[\alpha]_D^{20} = +25.4°$ (C=1% in methanol). m.p. 143°–146° C.

EXAMPLE 6

N-[d-2-(1-Hydroxy)-butyl]-d,l-2-(6-methoxy-2-naphthyl)-propionamide[d,d+l,d]

90 Grams (0.37 mole) of d,l-2-(6-methoxy-2-naphthyl)-propionic acid methyl ester were poured into 360 ml of anhydrous toluene, and the obtained mixture was refluxed for 30 minutes, whereby 45 ml of solvent were distilled off. After cooling to 90° C. and adding 45 ml (0.47 mole) of d-2-amino-1-butanol, the resulting solution was again refluxed for 30 minutes and further 45 ml of toluene were distilled off. The mixture was then cooled to 25° C. and added, under nitrogen atmosphere, with 8 ml (0.043 mole) of a 30% (w/w) methanol solution of sodium methoxide and stirred overnight at room temperature. After adding 180 ml of a 3% aqueous solution of hydrochloric acid and heating at 80° C. for 15 minutes, the reaction mixture was cooled to 5° C. and the solid which precipitated was filtered, washed first with water and then with toluene and finally dried in vacuo. 108 Grams (96%) of the title compound were obtained, identical with the product obtained as in Example 1. m.p. 105°–126.5° C.

EXAMPLE 7

N-[d-2-(1-Hydroxy)-butyl]-d,l-2-(6-methoxy-2-naphthyl)-propionamide[d,d+l,d]

The title compound was prepared substantially as described in the foregoing example, with the exception that the addition of sodium methoxide was carried out a 50° C. and the reaction mixture was stirred for two hours at this temperature, instead of overnight at room temperature. Yield (96%).

EXAMPLE 8

N-[d-2-(1-Hydroxy)-butyl]-d,l-2-(5-bromo-6-methoxy-2-naphthyl)-propionamide[d,d+l,d]

The title compound was prepared substantially according to the procedure described in Example 6, starting from 390 g (0.851 mole) of d,l-2-(5-bromo-6-methoxy-2-naphthyl)-propionic acid 3-bromo-2,2-dimethyl-propyl ester and 92 ml (0.97 mole) of d-2-amino-1-butanol. The amount of sodium methoxide corresponded to 15% (molar) of the starting d,l-ester. Yield: 300 g (93%) of a product with the same characteristics as that of Example 4. m.p. 143°–147° C.

EXAMPLE 9

N-[d-2-(1-Hydroxy)-butyl]-d,l-2-(5-bromo-6-methoxy-2-naphthyl)-propionamide[d,d+l,d]

The compound was prepared following the procedure of Example 7, starting from 119 g (0.37 mole) of d,l-2-(5-bromo-6-methoxy-2-naphthyl)-propionic acid methyl ester. Yield: 130 g (92.5%) of a product with the same characteristics as that of Example 4. m.p. 143°–147° C.

EXAMPLE 10

N-[d-2-(1-Hydroxy)-butyl]-d-2-(6-methoxy-2-naphthyl)-propionamide[d,d]

30 Grams (0.10 mole) of N-[d-2-(1-hydroxy)-butyl]-d,l-2-(6-methoxy-2-naphthyl)-propionamide, prepared as in any of Examples 1, 6 or 7, were suspended in 250 ml of toluene and the suspension was heated at the boling temperature of the solvent until a clear solution was obtained. 100 Milliliters of toluene were distilled off, then the solution was gradually cooled whereby, at about 85° C., the title compound begins to crystallize. Cooling was continued for 40 minutes and, at 60° C., the reaction suspension was added with 1,5 ml of a 30% (w/w) methanol solution of sodium methoxide and the mixture was kept at this temperature for 6 hours. The temperature was subsequently lowered to 52° C. in 1 hour, the suspension was kept at this temperature for 14 hours, then rapidly cooled to 45° C. and left standing for 6 hours. After filtering and washing with 60 ml of toluene, 26 g of the title compound, containing a small amount of the l,d isomer, determined by TLC, were obtained. Yield: 86.7%, calculated over the starting pair of diastereoisomeric amides. 15 Grams of the title product were recrystallized from 150 ml of toluene, thus obtaining 13.35 g (89%) of practically pure N-d-2-(1-hydroxy)-butyl]-d-2-(6-methoxy-2-naphthyl)-propionamide. M.p.=144°–145° C.; $[\alpha]_D^{20}= -34°$ (C=1% in methanol).

EXAMPLE 11 d-2-(6-Methoxy-2-naphthyl)-propionic acid

The amount of N-[d-2-(1-hydroxy)-butyl]-d-2-(6-methoxy-2-naphthyl)-propionamide obtained upon crystallization as described in the preceding Example was suspended in 70 ml of 6N aqueous hydrochloric acid and the resulting suspension was refluxed for 45 minutes. After adding 70 ml of water and cooling to 50° C., a solid precipitate formed, which was filtered and washed with water at 50° C. Yield: 10.20 g (94%) of the title substance; $[\alpha]_D^{20}= +65.3°$ (C=1% in chloroform), in agreement with the standards of the 1978 addendum to the British Pharmacopoeia of 1973.

EXAMPLE 12

N-[d-1-(Hydroxy)-butyl]-d-2-(6-methoxy-2-naphthyl)-propionamide [d,d]

The procedure of Example 10 was repeated, thus obtaining 27 g (90% over the starting pair of diastereoisomeric amides) of title compound, containing a small amount of the l,d diastereoisomer (TLC investigation). The above 27 g were recrystallized from 250 ml of toluene containing 1 ml of glacial acetic acid. Yield: 24.2 g of pure N-[d-1-(hydroxy)-butyl]-d-2-(6-methoxy-2-naphthyl)-propionic acid, with the same characteristics as those reported in Example 10.

The hydrolysis of the d,d -diastereoisomer, carried out as in Example 11, afforded d-2-(6-methoxy-2-naphthyl)-propionic acid with a 94% yield, with an $[\alpha]_D^{20}= +64.5°$ (C=1% in chloroform), again in agreement with the standards of the 1978 Addendum to the British pharmacopoeia 1973.

EXAMPLE 13

N-[d-1-(Hydroxy)-butyl]-d-2-(6-methoxy-2-naphthyl)-propionamide [d,d]

150 Grams (0.5 mole) of N-[d-(1-hydroxy)-butyl]-d,l-2(6-methoxy-2-naphthyl)-propionamide were dissolved under reflux in 1000 ml of toluene. After removing 250 ml of solvent by distillation, the reaction mixture was slowly cooled to 85° C., under nitrogen atmosphere, seeded with 0.5 g of the title compound, previously prepared, and further cooled to 70° C. in 60 minutes. 7.5 Milliliters of a 30% (w/w) methanol solution of sodium methoxide where then added, the whole was kept at this temperature for 4 hours, cooled to 60° C. in 1 hour and kept at this temperature overnight. The reaction mixture was subsequently treated with 5 ml of glacial acetic acid, heated to 105° C. and finally cooled to 45° C. in 3 hours. The obtained crystalline solid was recovered as described in Example 10 or 12. Yield: 132 g (88% with respect to the starting pair of diastereoisomeric amides) of practically pure title compound, having the same characteristics as the compound prepared under Example 10.

EXAMPLE 14 d-(2,6-Methoxy-2-naphthyl)-propionic acid

120 Grams (0.4 mole) of the compound prepared in the foregoing example, were suspended in a mixture of 560 ml of water and 88 ml of 48% (w/w) sulfuric acid, and the resulting suspension was heated under stirring at 98° C. for 11 hours.

After cooling to 60° C. and filtering, a solid was recovered, which was washed with water at 50° C., suspended in 500 ml of water and added with a 30% aqueous solution of sodium hydroxide until pH 10.5 was reached. The obtained solution was twice extracted with methylene chloride (100 ml ×2), the organic layer was discarded, the aqueous portion was added with 400 ml of water and filtered through dicalite. The clear filtrate was heated to 40° C., brought to pH 3.0 by means of 6N aqueous hydrochloric acid, whereby a solid precipitate formed. The whole was subsequently heated at 60° C. for 15 minutes, the solid was filtered, washed with 300 ml of water at 60° C. and finally dried in an oven. Yield: 84 g (91.3%) of a particularly pure title compound. $[\alpha]_D^{20}= +66.7°$ (C=1% in chloroform), in agreement with the standards as set forth in the 1978 Addendum to the British Pharmacopoeia of 1973.

EXAMPLE 15

N-[d-1-(Hydroxy)-butyl]-d-2-(6-methoxy-2-naphthyl)-propionamide [d,d]

60 Grams (0.24 mole) of d,l-2-(6-methoxy-2-naphthyl)-propionic acid methyl ester, 30 ml (0.32 mole) of d-2-amino-1-butanol and 5,5 ml (0.03 mole) of a 30% (w/w) methanol solution of sodium methoxide were poured into 360 ml of toluene under nitrogen atmosphere, and the resulting mixture was heated at 50° C. for 2 hours and, subsequently, for 15 hours at 60° C. 1.7 Milliliters of glacial acetic acid were added, the mixture was further heated until the solid completely dissolved, then the temperature was rapidly brought to 70° C. and the reaction solution seeded with 0.3 g of the title compound, previously prepared. In two hours, the reaction temperature was brought to 30° C., and the obtained crystalline solid was recovered by filtration and washed with toluene. Upon drying in vacuo, 62.5 g (84.6%, calculated over the starting d,l-ester), of the title compound in a practically pure form were obtained, having the same characteristics as the compound prepared under Example 10.

EXAMPLE 16

N-[l-2-(1-Hydroxy)-butyl]-l-2-(6-methoxy-2-naphthyl)-propionamide [l,l]

10 Grams (0.0332 mole) of N-[l-2-(1-hydroxy)-butyl]-d,l-2-(6-methoxy-2-naphthyl)-propionamide, prepared as in Example 2, were suspended in 100 ml di toluene added with 4 ml of triethylamine, and the resulting mixture was heated to 90° C. The temperature was then lowered in 1 hour and, at 83° C., the solution was seeded with 0.1 g of the title compound, previously prepared, and subsequently cooled to 40° C. in 2 hours. A crystalline solid was obtained, which was filtered, washed with toluene and dried. Yield: 4.4 g of practically pure title substance (88% over the amount of l,l-diastereoisomer present in the starting compound). M.p. 144°–145° C.$[\alpha]_D^{20}= -34.3°$ (C=1% in methanol)

EXAMPLE 17

N-[d-2-(1-Hydroxy)-butyl]-d-2-(5-bromo-6-methoxy-2-naphthyl)-propionamide [d,d]

10 Grams (0.0263 mole) of N-[d-2-(1-hydroxy)-butyl]-d,l-2-(5-bromo-6-methoxy-2-naphthyl)-propionamide, prepared as in any of Examples 4, 8 or 9, were suspended in 75 ml of N,N-dimethyl-formamide and 25 ml of water, the resulting suspension was heated until a clear solution was obtained, then the resulting solution was rapidly cooled to 35° C. At this temperature, 0.1 g of the title compound were added and the mixture was cooled in 4 hours to 10° C. The obtained crystalline solid was recovered by filtration, washed with 10 ml of a 3/1 (v/v) N,N-dimethylformamide/water solution and dried. Yield: 4 g practically pure title compound (80% over the amount of d,d isomer present in the starting material). M.p. 170°–171° C. $[\alpha]_D^{20} = -34.4°$ (C=1% in methanol).

EXAMPLE 18

N-[d-2-(1-Hydroxy)-butyl]-d-2-(5-bromo-6-methoxy-2-naphthyl)-propionamide [d,d]

10 Grams (0.0263 mole) of N-[d-2-(1-hydroxy)-butyl]-d,l-2-(5-bromo-6-methoxy-2-naphthyl)-propionamide, prepared as in any of Example 4, 8 or 9, were suspended in 100 ml of acetone and 50 ml of water, and the resulting suspension was heated to 40° C. At this temperature, the reaction mixture was added with 0.1 grams of the title compound, previously prepared, and cooled to 25° C. in 4 hours. The obtained crystalline solid was filtered, washed with 8 ml of a 2/1 (v/v) acetone/water mixture and finally dried. Yield: 4 g of practically pure title compound (80% over the amount of d,d isomer present in the starting material). m.p. 170°–171° C.

EXAMPLE 19 d-2-(5-Bromo-6-methoxy-2-naphthyl)-propionic acid

The title compound was obtained by operating substantially as described in Example 11, starting from 3.3 g (0.0087 mole) of N- d-2-(1-hydroxy)-butyl-d-2-(5-bromo-6-methoxy-2-naphthyl)-propionamide. Yield 2.6 g (96%). $[\alpha]_D^{20} = +45.5°$ (C=1% in chloroform).

EXAMPLE 20

N-[d-2-(1-Hydroxy)-butyl]-d-2-(6-methoxy-2-naphthyl)-propionamide [d,d]

30 Grams (0.0789 mole) of the amide prepared as in any of Examples 4, 8 or 9 was suspended in 60 ml of 2-methoxyethanol and 42 ml of water, and the resulting suspension was added with 11.8 ml of an aqueous 40% (w/v) solution of sodium hydroxide. The temperature was raised to 60° C., 1.2 g of Raney Nickel were added, the 5.7 ml of 100% aqueous hydrazine dissolved in 5.7 ml of water were slowly dripped into the reaction ambient. Once the addition was terminated, the catalyst was removed by filtration and the filtrate was kept for 1 hour at 50° C. Upon cooling to 40° C., a solid precipitated, which was filtered, washed with water and dried. Yield: 10.2 g (43%) of N-[d-2-(1-hydroxy)-butyl]-d-2-(6-methoxy-2-naphthyl)-propionamide.

Starting substrate of formula II which can be employed in the present invention are:

d,l-2-(6methoxy-2-naphthyl)-propionic acid butyl ester
d,l-2-(6-methoxy-2-naphthyl)-propionic acid hexyl ester
d,l-2-(6-methoxy-2-naphthyl)-propionic acid heptyl ester
d,l-2-(6-methoxy-2-naphthyl)-propionic acid neopentyl ester
d,l-2-(6-methoxy-2-naphthyl)-propionic acid 3-bromo-2,2-dimethyl-propyl ester
d,l-2-(5-bromo-6-methoxy-2-naphthyl)-propionic acid 2-bromoethyl ester
d,l-2-(5-bromo-6-methoxy-2-naphthyl)-propionic acid, (3-bromo-2-methyl-2-propyl)-propyl ester.
d,l-2-(6-methoxy-2-naphthyl)-propionic acid, (3-bromo-2-methyl-2-propyl)-propyl ester
d,l-2-(5-bromo-6-methoxy-2-naphthyl)-propionic acid, (3-bromo-2-methyl-2-isopropyl)-propyl ester
d,l-2-(6-methoxy-2-naphthyl)-propionic acid, (3-bromo-2-methyl-2-isopropyl)-propyl ester
d,l-2-(5-bromo-6-methoxy-2-naphthyl)-propionic acid, (3-bromo-2-methyl-2-phenyl)-propyl ester
d,l-2-(6-methoxy-2-naphthyl)-propionic acid, (3-bromo-2-methyl-2-phenyl)-propyl ester
d,l-2-[(butyryloxy)carbonyl]-2-(6-methoxy-2-naphthyl)-ethane
d,l-2-[(benzoyloxy)carbonyl]-2-(6-methoxy-2-naphthyl)-ethane
d,l-2-[(benzoyloxy)carbonyl]-2-(5-bromo-6-methoxy-2-naphthyl)-ethane By operating substantially according to the amidation procedure described in the foregoing examples, the following pairs of diastereoisomeric amides can be prepared N-[d-2-(1-hydroxy)-pentyl)]-d,l-2-(6-methoxy-2-naphthyl)-propionamide
N-[d-2-(1-hydroxy-4-methyl)-pentyl]-d,l-2-(6-methoxy-2-naphthyl)-propionamide
N-[d-2-(1-(hydroxy)-hexyl]-d,l-2-(6-methoxy-2-naphthyl)-propionamide
N-[l-2-(hydroxy)-pentyl]-d,l-2-(6-methoxy-2-naphthyl)-propionamide
N-[d-1-(2-hydroxy)-butyl]-d,l-2-(6-methoxy-2-naphthyl)-propionamide
N-[d-2-(3,3-dimethyl-1-hydroxy)-butyl]-d,l-2-(6-methoxy-2-naphthyl)-propionamide
N-[d-2-(1-hydroxy)-octyl]-d,l-2-(6-methoxy-2-naphthyl)-propionamide
N-[d-1-(2-hydroxy)-hexyl]-d,l-2-(6-methoxy-2-naphthyl)-propionamide
N-[d-2-[1-hydroxy-2-(4-hydrophenyl)]-ethyl]-d,l-2-(6-methoxy-2-naphthyl)-propionamide
N-[l-2-[1-hydroxy-2-(4-hydroxyphenyl)]-ethyl]-d,l-2-(6-methoxy-2-2-naphthyl)-propionamide
N-[d-2-(1-hydroxy-2-naphthyl-1-yl)-ethyl]-d,l-2-(6-methoxy-2-naphthyl)-propionamide
N-[l-2-(1-hydroxy-2-naphthyl-1-yl)-ethyl]-d,l-2-(6-methoxy-2-naphthyl)-propionamide
N-[d-1-[2-hydroxy-2-(4-hydroxyphenyl)]-ethyl]-d,l-2-(6-methoxy-2-naphthyl)-propionamide
N-[d-2-(1-hydroxy)-propyl]-d,l-2-(5-bromo-6-methyl-2-naphthyl)-propionamide
N-[d-2-(1-hydroxy-3-methyl)-butyl]-d,l-2-(5-bromo-6-methoxy-2-naphthyl)-propionamide
N-[d-2-(1-hydroxy-4-methyl)-pentyl]-d,l-2-(5-bromo-6-methoxy-2-naphthyl)-propionamide
N-[l-2-(1-hydroxy-4-methyl)-pentyl]-d,l-2-(5-bromo-6-methoxy-2-naphthyl)-propionamide
N-[l-2-(1-hydroxy)-heptyl]-d,l-2-(5-bromo-6-methoxy-2-naphthyl)-propionamide
N-[l-2-[1-hydroxy-2-(4-hydroxyphenyl)]-ethyl]-d,l-2-(5-bromo-6-methoxy-2-naphthyl)-propionamide
N-[l-2-[1-hydroxy-1-(4-hydroxy-3-methoxyphenyl)]-ethyl]-d,l-2-(5-bromo-6-methoxy-2-naphthyl)-propionamide The pair of diastereoisomeric amides can be resolved into the corrsponding single diastereoisomeric amides as illustrated in the foregoing examples.

We claim:

1. A process for the optical resolution of a racemic mixture of an α-naphthyl-propionic acid of formula

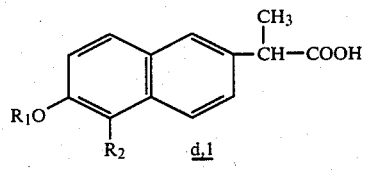

I wherein $R_1$ is $(C_{1-6})$alkyl and $R_2$ is hydrogen, halogen, mercapto, $(C_{1-6})$alkylthio, phenylthio, benzylthio, $(C_{1-6})$alkylsulfonyl, benzenesulfonyl or benzenesulfonyl substituted by halogen or $(C_{1-4})$ alkyl, which comprises the steps of:

(A) reacting a substantially racemic substrate of formula

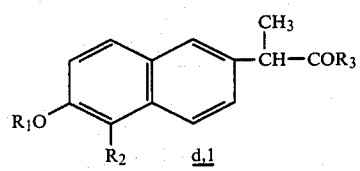

II wherein $R_1$ and $R_2$ are as defined hereinabove and $R_3$ is a member selected from the group consisting of hydroxy, $(C_{1-8})$alkoxy, $(C_{1-8})$alkoxy substituted by at least one of halogen and phenyl, $(C_{2-6})$aliphatic acyloxy, benzoyloxy, substituted benzoyloxy, sulfonyloxy, $(C_{1-6})$alkyl-sulfonyloxy, benzenesulfonyloxy, 4-methyl-benzenesulfonyloxy, 2-imidazol-carbonyloxy and halogen, with a compound of formula $R_4$—$NH_2$   III in which $R_4$ is the residue of a primary or secondary alcohol which together with the —$NH_2$ radical, forms an optically active β-aminoalcohol, and is a member selected from the group consisting of

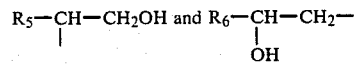

wherein $R_5$ is $(C_{1-6})$alkyl, primary hydroxy $(C_{1-4})$-alkyl, mercaptomethyl, methylthioethyl, phenyl, hydroxyphenyl, phenylmethyl, hydroxyphenylmethyl, naphthyl, indolyl and imidazolyl, and $R_6$ is $(C_{1-6})$alkyl, phenyl, hydroxyphenyl, di-hydroxyphenyl and (4-hydroxy-3-methoxy)-phenyl, in the proportion of 1 mole of said compound II with 1-10 moles of said compound III, at a temperature between room temperature and the boiling temperature of the reaction mixture, thus obtaining a pair of diastereoisomeric amides of formula

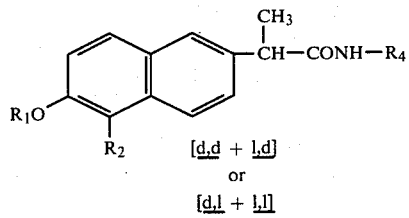

IV wherein $R_1$, $R_2$ and $R_4$ are as defined hereinabove;

(B) resolving said pair of diastereoisomeric amides into the single diastereoisomeric amides by preparing a hot solution of said pair of diastereoisomeric amides in an inert organic solvent, or a mixture thereof with water, gradually lowering the temperature of the solution until complete precipitation of the less soluble single diastereosiomeric amide of formula

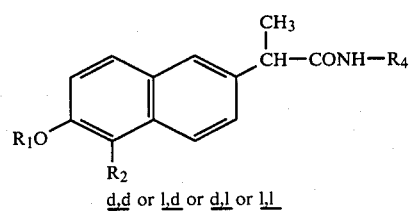

V wherein $R_1$, $R_2$ and $R_4$ are as defined hereinabove.

(C) subjecting the obtained single diastereoisomeric amide to acid hydrolysis, thus recovering a compound of formula

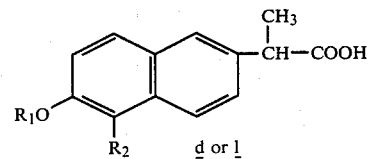

VI in which $R_1$ and $R_2$ are as defined hereinabove.

2. The process according to claim 1 wherein $R_3$ in said substrate of formula II is halogen and said step A is carried out at room temperature.

3. The process according to claim 1 wherein $R_3$ in said substrate of formula II is selected from the group consisting of hydroxy, $(C_{1-8})$alkoxy, $(C_{1-8})$alkoxy substituted by at least one of halogen and phenyl, $(C_{2-6})$aliphatic acyloxy, benzoyloxy, substituted benzoyloxy, sulfonyloxy, $(C_{1-6})$alkyl-sulfonyloxy, benzenesulfonyloxy, 4-methyl-benzenesulfonyloxy, and 2-imidazolyl-carbonyloxy and said step A is carried out in an inert organic solvent at a temperature up to the boiling point of the reaction mixture.

4. The process as defined in claim 1, wherein in the said substrate of formula II, $R_1$ is $(C_{1-6})$alkyl, $R_2$ is hydrogen or halogen, and $R_3$ is a member selected from the group consisting of hydroxy, $(C_{1-8})$alkoxy, $(C_{1-8})$alkoxy substituted by at least one of phenyl and halogen, $(C_{2-6})$aliphatic acyloxy, benzoyloxy and halogen.

5. The process according to claim 1 wherein the reactants of formula II and III in step A are contacted in the presence of a strong basic agent in the amount of 3 to 15 molar percent with respct to said compound of formula II and wherein the strong basic agent is ammonium hydroxide, an alkali metal or alkaline earth metal hydride or amide, or an alkali metal ($C_{1-4}$)alkoxide.

6. The process according to claim 5, wherein the basic agent is an alkali metal ($C_{1-4}$)alkoxide.

7. The process according to claim 4, wherein, in said substrate of formula II, $R_1$ is ($C_{1-6}$)alkyl, $R_2$ is hydrogen or halogen and $R_3$ is ($C_{1-8}$)alkoxy, ($C_{1-8}$)alkoxy substituted by at least one of halogen and phenyl or halogen.

8. The process according to claim 1, wherein, in the optically active β-aminoalcohol of formula $R_4$—$NH_2$, $R_4$ is

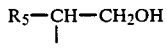

or the group

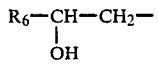

and $R_5$ and $R_6$ are ($C_{1-6}$)alkyl.

9. A process according to claim 8, wherein, in the optically active β-aminoalcohol of formula $R_4$—$NH_2$, $R_4$ is

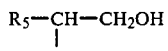

and $R_5$ is ethyl.

10. The process according to claim 2 wherein said step A is carried out in the presence of an organic base to neutralize the acid formed in the reaction.

11. The process according to claim 1, wherein said step A is carried out in the presence of an inert organic solvent which is a member selected from the group consisting of ($C_{6-9}$)linear or cyclic hydrocarbons, aromatic hydrocarbons, halogenated ($C_{1-4}$)hydrocarbons, tetrahydrofuran, dihydropyran, tetrahydropyran, ethylene glycol and propylene glycol and their corresponding mono- or di-($C_{1-2}$)alkyl ethers, lower aliphatic ketones, ethyl acetate, butyl acetate, and mixtures thereof.

12. The process according to claim 11, wherein the inert organic solvent is an aromatic hydrocarbon or a halogenated ($C_{1-4}$)hydrocarbon.

13. The process according to claim 1, wherein the solvent in step (B) is a member selected from the group consisting of ($C_6$-$C_9$)linear or cyclic hydrocarbons, aromatic hydrocarbons, halogenated ($C_{1-4}$)hydrocarbons, ($C_{1-6}$)lower alkanols, tetrahydrofuran, dihydropyran, tetrahydropyran and mixture thereof, ethylene glycol and propylene glycol and their corresponding mono- or di-($C_{1-2}$)alkyl ethers, lower aliphatic ketones, ethyl acetate, butyl acetate, and mixtures thereof, a mixture of a lower aliphatic ketone and water, N,N-di-(lower alkyl)-amides of lower aliphatic acids and mixtures thereof with water.

14. The process according to claim 13, wherein the solvent is an aromatic hydrocarbon, a ($C_{1-6}$)lower alkanol, a halogenated ($C_{1-4}$)hydrocarbon, a lower aliphatic ketone, an N,N-di-(lower alkyl)-amide of a lower aliphatic acid, a mixture of said N,N-di(lower alkyl)amide with water, or 2-methoxyethanol.

15. The process according to claim 14, wherein the solvent is an aromatic hydrocarbon, a ($C_{1-6}$)lower alkanol, or a halogenated ($C_{1-4}$)hydrocarbon.

16. The process according to claim 1 wherein step (B) is carried out in the presence of a basic reagent which is ammonium hydroxide, an metal lower alkoxide, an metal or alkaline earth metal hydride or amide in amount between 3 and 10 mole percent with respect to the pair of diastereoisomeric amides.

17. The process according to claim 16, wherein the basic reagent is a lower alkali metal alkoxide.

18. The process according to claim 1 wherein the solution of the pair of diastereoisomeric amides in step (B) is seeded with the less soluble single diastereoisomeric amide.

19. The process according to claim 1, wherein the pair of diastereoisomeric amides prepared in step (A) is directly resolved into the single diastereoisomeric amides in step (B).

20. The process according to claim 1, wherein the hydrolysis of the single diastereoisomeric amide in step (C) is carried out by means of concentrated or dilute mineral acid.

21. The process according to claim 1, wherein $R_2$ is halogen, mercapto, ($C_{1-6}$)alkylthio, phenylthio, benzylthio, ($C_{1-6}$)alkylsulfonyl, benzenesulfonyl or benzenesulfonyl substituted by halogen (or $C_{1-4}$)alkyl, said $R_2$ is replaced by hydrogen by hydrogenation of said pairs of said stereoisomeric acids obtained in step (A) and resolution of said pairs of said steroisomeric amides is obtained simultaneously.

22. A compound of formula

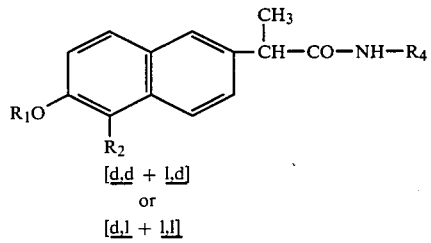

wherein $R_1$ is ($C_{1-6}$)alkyl, $R_2$ is hydrogen, halogen, mercapto, ($C_{1-6}$)alkylthio, pheylthio, benzylthio, ($C_{1-6}$)alkylsulfonyl, benzenesulfonyl or benzenesulfonyl substituted by halogen or ($C_{1-4}$)alkyl and $R_4$ is

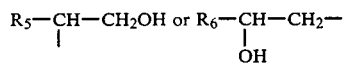

wherein $R_5$ is ($C_{1-6}$)alkyl, primary hydroxy ($C_{1-4}$)alkyl, mercaptomethyl, methylthioethyl, phenyl, hydroxyphenyl, phenylmethyl, hydroxyphenylmethyl, naphthyl, indolyl and imidazolyl, and $R_6$ is ($C_{1-6}$)alkyl, phenyl, hydroxyphenyl, di-hydroxyphenyl or (4-hydroxy-3-methoxy)-phenyl.

23. A compound of formula

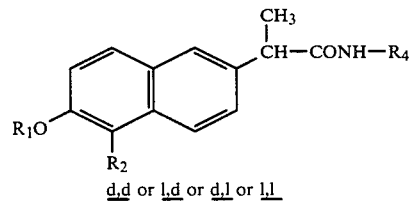

wherein $R_1$ is a $(C_{1-6})$alkyl, $R_2$ is hydrogen, halogen, mercapto, $(C_{1-6})$alkylthio, phenylthio, benzylthio, $(C_{1-6})$alkylsulfonyl, benzenesulfonyl or benzenesulfonyl substituted by halogen or $(C_{1-4})$alkyl and $R_4$ is

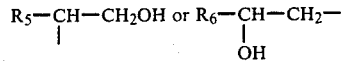

wherein $R_5$ is $(C_{1-6})$alkyl, primary hydroxy $(C_{1-4})$alkyl, mercaptomethyl, methylthioethyl, phenyl, hydroxyphenyl, phenylmethyl, hydroxyphenylmethyl, naphthyl, indolyl and imidazolyl, and $R_6$ is $(C_{1-6})$alkyl, phenyl, hydroxyphenyl, di-hydroxyphenyl or (4-hydroxy-3-methoxy)-phenyl.

24. A compound according to claim 22 wherein $R_1$ is $(C_{1-6})$alkyl, $R_2$ is hydrogen or halogen, $R_4$ is

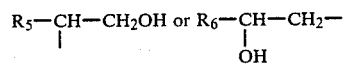

and $R_5$ and $R_6$ are $(C_{1-6})$-alkyl.

25. A compound according to claim 22 wherein $R_1$ is $(C_{1-6})$alkyl, $R_2$ is hydrogen or halogen, $R_4$ is

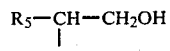

and $R_5$ is ethyl.

26. A compound according to claim 23 wherein $R_1$ is $(C_{1-6})$alkyl, $R_2$ is hydrogen or halogen, $R_4$ is

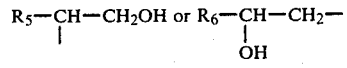

and $R_5$ and $R_6$ are $(C_{1-6})$-alkyl.

27. A compound according to claim 23 wherein $R_1$ is $(C_{1-6})$alkyl, $R_2$ is hydrogen or halogen, $R_4$ is

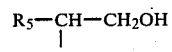

and $R_5$ is ethyl.

* * * * *